United States Patent [19]

Khosla et al.

[11] Patent Number: 5,998,369
[45] Date of Patent: Dec. 7, 1999

[54] TREATMENT OF OSTEOPOROSIS

[75] Inventors: Sundeep Khosla; Cheryl A. Conover, both of Rochester, Minn.

[73] Assignee: Mayo Foundation for Medical Education and Research, Rochester, Minn.

[21] Appl. No.: 09/073,032

[22] Filed: May 5, 1998

Related U.S. Application Data

[60] Provisional application No. 60/045,607, May 5, 1997, abandoned.

[51] Int. Cl.[6] ............................ A61K 38/30; A61K 38/00
[52] U.S. Cl. .................................. 514/12; 514/2; 514/21; 536/23.4; 536/23.51; 530/350; 530/399
[58] Field of Search ................................ 536/23.4, 23.51; 435/69.1, 69.7, 320.1, 252.33; 530/350, 399; 514/2, 12

[56] References Cited

U.S. PATENT DOCUMENTS

| 5,187,151 | 2/1993 | Clark et al. | 514/12 |
| 5,569,648 | 10/1996 | Lewis et al. | 514/12 |
| 5,681,818 | 10/1997 | Spencer et al. | 514/12 |

FOREIGN PATENT DOCUMENTS 0 259 904   3/1988   European Pat. Off. .

OTHER PUBLICATIONS

Dull et al., *Nature*, 310, pp. 777–781 (1984).
Bell et al., *Nature*, 310, pp. 775–777 (1984).
Beyer et al., *J. Bone Min. Res.*, 5:1257–1263 (1990).
Conover, C.A. *J. Bone Min. Res.*, 1st Edition, Blezikian, J.P. et al., Editors, San Diego, Academic Press (1996), pp. 607–618.
Conover, C.A., *J. Clin. Invest.*, 88:1354–1361 (1991).
Diamond et al., *Bone*, 19:679–683 (1996).
Ebeling et al., *J. Clin. Endocrinol.*, 77:1384–1387 (1993).
Ghiron et al., *J. Bone Miner. Res.*, 10:1844–1852 (1995).
Hassoun et al., *Am. J. Med.*, 103:70–73 (1997).
LeRoith, *New Engl. J. Med.*, 336:633–640 (1997).
Liu et al., *J. Clin. Endocrinol. Metab.*, 75:1261–1267 (1992).
Liu et al., *J. Clin. Endocrinol. Metab.*, 76:1095–1100 (1993).
Valenzano et al., *J. Biol. Chem.*, 272:4804–4813 (1997).
Villareal et al., *Am. J. Med.*, 93:371–381 (1992).
Whyte et al., *Am. J. Med.*, 102:219–220 (1997).
Whyte et al., *J. Bone Miner. Res.*, 11:554–558 (1996).
Glaser et al., *Spine*, 22:12S–16S (1997).
Adams et al., *Endocrine Society*, 1997 meeting, Abst. P3–240, p. 496.
Dull et al., *Nature*, 310, pp. 777–781, Aug. 30, 1984.

*Primary Examiner*—F. T. Moezie
*Attorney, Agent, or Firm*—Fish & Richardson, P.C. P.A.

[57] ABSTRACT

A substantially pure complex including IGFIIE polypeptide and IGFBP2 polypeptide is described. Methods for treating an osteoporosis patient and targeting a compound to the skeletal extracellular matrix of a patient are also described.

13 Claims, 3 Drawing Sheets

5,998,369

TREATMENT OF OSTEOPOROSIS

CROSS REFERENCE TO RELATED APPLICATIONS

This application claims priority from U.S. Provisional Application Ser. No. 60/045,607, filed May 5, 1997 now abandoned.

STATEMENT AS TO FEDERALLY SPONSORED RESEARCH

Funding for the work described herein was provided by the federal government, which may have certain rights in the invention.

BACKGROUND OF THE INVENTION

Hepatitis C-associated osteosclerosis (HCAO) is a rare syndrome characterized by a marked increase in skeletal mass in adults who are infected with the hepatitis C virus. Beyer et al., *J. Bone Min. Res.*, 5:1257–1263 (1990); and Diamond et al., *Bone*, 19:679–683 (1996). Spine and hip bone mineral densities are elevated as much as two-fold in these affected individuals, who represent the most dramatic example of acquired osteosclerosis in humans. Radiographs show dense bones in the appendicular and axial skeleton, with sparing of the calvarium and facial bones. Biochemical markers of bone formation are usually elevated, and transiliac bone biopsies generally show increased bone formation rates. Nevertheless, osseous tissue from these patients appears histologically to be of good quality with intact lamellar patterns, unlike the abnormal, rapidly remodeling woven bone found in patients with Paget's bone disease.

To date, ten cases of HCAO have been reported. It is apparent, however, that only a small percentage of all patients infected with hepatitis C develop osteosclerosis, since skeletal radiographs of 107 randomly selected hepatitis C infected patients failed to show dense bones. Beyer et al., *Am. J. Med.*, 95:660–662 (1990). Thus, although it is uncertain whether hepatitis C is the causative agent of the skeletal disease, a plausible hypothesis is that either hepatitis C or another parenterally transmitted agent increases hepatic production of a growth factor(s) that stimulate osteoblast function.

SUMMARY OF THE INVENTION

The invention is based on the discovery that insulin-like growth factor binding protein 2 (IGFBP2) facilitates targeting of insulin-like growth factors (IGFs), and in particular, IGFIIE, to skeletal tissue. Complexes of IGFIIE polypeptide and IGFBP2 polypeptide are effective in stimulating human osteoblast proliferation and can be used for increasing bone mass in patients with osteoporosis.

The invention features a substantially pure complex including an IGFIIE polypeptide and an IGFBP2 polypeptide. IGFIIE polypeptide and IGFBP2 polypeptide can be present in approximately equimolar amounts. The IGFBP2 polypeptide can be full-length IGFBP2.

The invention also features a method of treating an osteoporosis patient. The method includes administering an amount of a complex including an IGFII polypeptide and an IGFBP2 polypeptide effective to increase bone mass in the patient. IGFBP2 polypeptide can be full-length IGFBP2. IGFII polypeptide can be IGFII or IGFIIE.

The invention also relates to a method of targeting a compound to skeletal extracellular matrix of a patient. The method includes administering a complex to the patient. The complex includes an IGFIIE polypeptide, an IGFBP2 polypeptide and the compound. The IGFBP2 polypeptide can be full-length IGFBP2. The compound includes a chemotherapeutic agent or a growth factor such as an IGFII polypeptide or IGFI. IGFIIE is a particularly useful IGFII polypeptide.

The invention also features a pharmaceutical composition including a complex including IGFII polypeptide and IGFBP2 polypeptide in an amount effective to increase bone mass in a mammal and a pharmaceutically acceptable carrier.

The invention also features an article of manufacturing including packaging material and a pharmaceutical agent contained within the packaging material. The pharmaceutical agent includes a complex including an IGFII polypeptide and an IGFBP2 polypeptide and is therapeutically effective for increasing bone mass. The packaging material includes a label or package insert indicating that the pharmaceutical agent can be used for increasing bone mass or treating osteoporosis.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Substantially Pure Complexes

Figure 1:
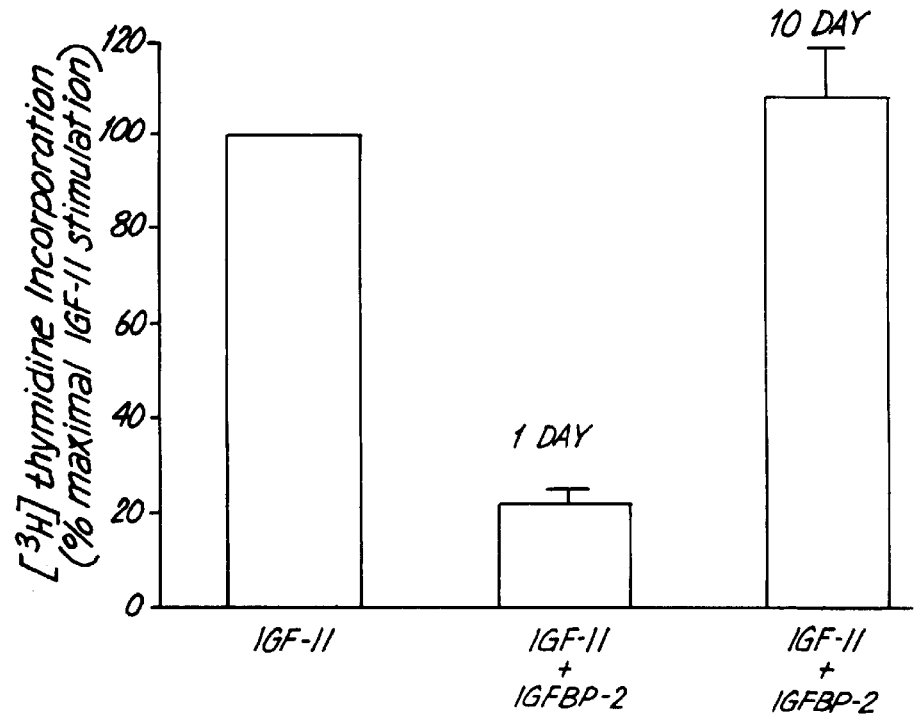
FIG. 1 is a chromatogram of IGFIIE levels from sera of two HCAO patients (♦—♦, ■—■) and from a normal control subject (▲—▲). The arrows indicate the elution volume of proteins used as molecular size markers, with the numbers indicating the size in kD.

In one aspect, the invention features a substantially pure complex including an IGFIIE polypeptide and an IGFBP2 polypeptide. Substantially pure complexes including IGFIIE polypeptide and IGFBP2 polypeptide are readily formed upon incubation of the purified polypeptides with each other. A complex containing approximately equimolar amounts of IGFIIE polypeptide and IGFBP2 polypeptide is particularly usefull. IGFII is a skeletal growth factor that is produced by the liver and by osteoblasts. Conover, In *Principles of Bone Biology*, 1st Edition, J. P. Bilezikian, L. G. Raisz, and G. A. Rodan, editors, Academic Press/San Diego, pp 607–618 (1996); and LeRoith, *New Engl. J. Med.*, 336:633–640 (1997). IGFII is synthesized as a precursor with a carboxy-terminal E-domain extension. This prohormone (IGFIIE) is then processed, by removal of the E-domain, into a mature ~7 kD peptide normally present in the circulation. IGFIIE appears to have biologic activity similar to IGFII, and increased circulating levels of ~10–20 kD IGFIIE produced by certain mesenchymal and epithelial tumors have been implicated in the pathogenesis of nonislet cell tumor hypoglycemia (NICTH)). Valenzano et al., *J. Biol. Chem.*, 272:48004–4813 (1997); and Liu et al., *J. Clin. Endocrinol. Metab.*, 76:1095–1100 (1993).

As used herein, the term "polypeptide" relates to the specific polypeptide of interest and polypeptides that are fuinctionally equivalent to the specific polypeptide. For example, IGFIIE polypeptide includes IGFIIE and polypeptides that are functionally equivalent to IGFIIE. IGFBP2 polypeptide includes IGFBP2 and polypeptides that are functionally equivalent to IGFBP2. Functionally equivalent polypeptides retain the biological activity of the specific polypeptide and can contain amino acid insertions, deletions or substitutions, as well as chemical modifications. Functionally equivalent polypeptides are readily identified using the methods described herein.

Amino acid insertions can include, for example, glycosaminoglycan binding motifs such as a heparin binding motif. Amino acid deletions can include, for example, regions of the polypeptide that are not required for binding or binding specificity. Amino acid substitutions can include conservative and non-conservative amino acid substitutions. Conservative amino acid substitutions replace an amino acid with an amino acid of the same class, whereas non-conservative amino acid substitutions replace an amino acid with an amino acid of a different class. Non-conservative substitutions may result in a change in the hydrophobicity of the polypeptide or in the bulk of a residue side chain. In addition, non-conservative substitutions may make a substantial change in the charge of the polypeptide, such as reducing electropositive charges or introducing electronegative charges. Nevertheless, such changes are possible if the resulting peptide retains the biological activity of the unmodified polypeptide. Examples of non-conservative substitutions include a basic amino acid for a non-polar amino acid, or a polar amino acid for an acidic amino acid. Amino acid insertions, deletions and substitutions can be made using random mutagenesis, site-directed mutagenesis or other recombinant techniques known in the art.

IGFIIE polypeptide can be produced through standard recombinant techniques. The cDNA of IGFIIE has a GenBank accession number of X00910 M17862 g32995. Bell, G.I. et al., *Nature*, 310(5980):775–777 (1984). In bacterial systems, IGFIIE is isolated from inclusion bodies solubilized in approximately 8M urea. After refolding of the protein, standard chromatographic techniques are used to purify IGFIIE.

The IGFBPs are high affinity binding proteins that modulate the activity of IGFs both systemically and locally. Six IGFBPs have been characterized. The IGFBPs are structurally homologous yet functionally distinct, and serve a number of roles, including transport of IGFs in the circulation, delivery of IGFs to target tissues, and modulation of cell responses to IGFs. Ninety-five percent of IGFs in the circulation are tightly bound to IGFBP3 with an acid labile subunit (ALS) in a ternary complex of ~150 kD. This 150 kD complex is restricted to the vascular space and serves to limit bioavailability of IGFs to target tissues. Approximately 5% of IGFs circulate bound to IGFBP-1, -2, and -4 in ~50 kD binary complexes, which can cross the capillary barrier and may be responsible for targeting IGFs to specific tissues.

Human IGFBP2 can be purchased from Sandoz Pharmaceuticals (Basel, Switzerland) or Austral (San Ramon, Calif.). Alternatively, IGFBP2 can be produced by standard recombinant techniques. The coding sequence for human IGFBP2 has a GenBank accession number of M35410 g179476. Agarwal, N. et al., *Exp. Eye Res.*, 52(5):549–561 (1991). The coding sequence for bovine IGFBP2 is also available. Upton, F. Z. et al., *J. Mol. Endocrinol.*, 5:77–84 (1990). In general, IGFBP2 can be isolated from conditioned cell media by affinity chromatography with human IGFI protein coupled to Affi-prep 10 media or similar solid support materials and subsequently purified by chromatographic techniques.

Methods for Treating Osteoporosis

The invention also features a method of treating an osteoporosis patient. The method includes administering an amount of a complex including an IGFII polypeptide and an IGFBP2 polypeptide effective to increase bone mass in the patient. Osteoporosis is a skeletal condition characterized by decreased density of normally mineralized bone, leading to an increased number of fractures. Post-menopausal, age-related and idiopathic osteoporosis are non-limiting examples of primary osteoporosis that can be beneficially treated using this method. Secondary forms of osteoporosis caused by, for example, excessive alcohol intake, hypogonadism, hypercortisolism and hyperthyroidism can also be treated using this method. IGFII and IGFIIE are particularly useful IGFII polypeptides.

A number of anti-resorptive drugs, including estrogen, calcitonin, bisphosphonates, and selective estrogen receptor modulators are now available to treat osteoporosis, although the ability to achieve large, sustained increases in bone mass remains an elusive goal. HCAO is associated with marked increases in bone mass in adult life, which may be related to specific abnormalities in the IGF/IGFBP system. HCAO patients have normal serum levels of IGFI and -II, but have markedly elevated levels of IGFIIE. Of the IGFBPs, an increase in IGFBP2 was unique to these patients and was not found in control hepatitis C or hepatitis B patients. IGFI and -II in sera from patients with HCAO were carried, as in the case of sera from control subjects, bound to IGFBP3 in the ~150 kD complex, which is retained in the circulation. IGFIIE, however, was predominantly in a ~50 kD complex in association with IGFBP2; this complex can cross the capillary barrier and access target tissues. In vitro, IGFII enhanced recombinant human IGFBP2 binding by over 3-fold to extracellular matrix produced by human osteoblasts and in an extracellular matrix-rich environment, the IGFII/IGFBP2 complex was as effective as IGFII alone in stimulating human osteoblast proliferation. Thus, IGFBP2 may facilitate the targeting of IGFs, and in particular IGFIIE, to skeletal tissue in HCAO patients, with a subsequent stimulation by IGFs of osteoblast function. The present finding with respect to HCAO suggests an approach to increase bone mass in patients with osteoporosis. Longitudinal data spanning three years in one of the patients provide support for a cause-and-effect relationship between the elevated IGFBP2 and IGFIIE levels and the increase in bone formation.

Increases in both IGFBP2 and IGFIIE may be required for the stimulation of bone formation observed in HCAO patients. Thus, patients with hepatitis C but without osteosclerosis, and patients with Paget bone disease, had elevated IGFIIE immunoreactivity but normal IGFBP2 levels. IGFBP2 levels also are elevated following long term fasting, in association with certain tumors, and in advanced cirrhotic liver disease. None of these conditions is associated with osteosclerosis as found in the HCAO patients. A common genotype or novel strain of hepatitis C was not observed in four of the seven HCAO patients.

It should be noted that measurements of IGFIIE in serum (~10–20 kD) were based on standard curves using the E-II$_{69-84}$ fragment (1.8 kD). Furthermore, while the antibody generated against E-II$_{69-84}$ specifically recognized the IGFIIE prohormone, it does not appear to have full access to this epitope in the larger IGFIIE precursor form. Recombinant IGFIIE consisting of IGFII plus the first 21 amino acids of the E-peptide domain is only 3–17% as effective an antigen as the E-II$_{69-84}$ peptide in the IGFII E-domain RIA. Thus, on a molar basis, conservative estimates of circulating levels of intact IGFIIE in HCAO patients would equal or exceed levels of IGFBP2 (~24 nM).

The only other known disorder associated with both IGFBP2 and IGFIIE elevations is NICTH. NICTH patients develop severe hypoglycemia, and although bone mass or bone turnover have not been assessed in these individuals, they have not been reported to have osteosclerosis. Conversely, none of the patients with HCAO has had clinically evident hypoglycemia. Indeed, two of the HCAO patients had diabetes mellitus and received therapy with either an oral agent or with insulin and serum fasting glucose concentrations in at least six of the patients have not been low.

The primary cause of hypoglycemia in NICTH appears to be the ability of tumor-derived IGFIIE to directly and indirectly impair formation of the 150 kD ternary IGF/IGFBP3/ALS complex (i.e., by decreasing growth hormone and growth hormone-dependent ALS). In contrast, formation of the 150 kD complex is not impaired in HCAO, with all of IGFI and the majority of IGFII remaining tightly bound to IGFBP3 in the ternary complex, as in the case of normal serum. Production of IGFIIE and IGFBP2 by the same tissue (i.e., the liver) and rapid formation of a complex, may not disturb the normal IGF/IGFBP pattern, explaining an absence of hypoglycemia in HCAO patients.

Under conditions in which extracellular matrix is present, an equimolar IGFII/IGFBP2 complex was as effective as IGFII in stimulating osteoblast proliferation. In contrast, several previous studies indicated that IGFBP2 can inhibit IGF action. There are, however, important differences between these studies and the in vivo and in vitro findings described herein. The inhibitory effect of IGFBP2 on IGFI stimulation of osteoblast function was demonstrated by a 10-fold or greater molar excess of IGFBP2 relative to IGFI. Circulating levels of intact IGFIIE in HCAO patients would equal or exceed levels of IGFBP2; hence, IGFBP2 would not be in significant molar excess in HCAO patients. When equimolar amounts of IGFBP2 and IGFII were used, IGFBP2 was not inhibitory in the ten day cultures. Thus, both the concentration of IGFBP2 used and the presence or absence of extracellular matrix appear to be important factors in determining IGFBP2 effects on IGF bioavailability. A similar situation appears to be present in the case of IGFBP3, which can inhibit IGF action, but IGFBP3 at low concentrations or cell-associated IGFBP3 is not inhibitory for IGFI effects. In addition, IGFBP-5 binding to extracellular matrix results in decreased affinity of IGFBP-5 for IGFs, thus increasing the bioavailability of IGFs.

IGFI has been used as a treatment for osteoporosis and increased levels of markers of bone formation were observed in the serum. This approach was limited, however, by multiple systemic effects of IGFI, including hypoglycemia. Ebeling, P. R. et al., *J. Clin. Endocrinol.*, 77:1384–1387 (1993); Ghyon, L. S., et al., *J. Bone Miner. Res.*, 10:1844–1852 (1995). A combination of IGFI and IGFBP3 has been administered to health elderly females, permitting administration of higher doses of IGFI. An increase in bone formation indices was noted in this study. Adam, S. et al., *Endocrine Society*, 1997 meeting, Abst. P3–240, p. 496. The present results indicate that a more efficient transfer of IGFs to the skeleton can be accomplished using IGFBP2 polypeptide, and in particular, a complex including IGFIIE polypeptide and IGFBP2 polypeptide.

The invention also features a method of targeting a compound to the skeletal extracellular matrix of a patient. The method includes administering a complex of an IGFIIE polypeptide, an IGFBP2 polypeptide and the compound to the patient. Non-limiting examples of compounds include chemotherapeutic agents and growth factors such as a IGFI.

As shown herein, IGFBP2 and IGFIIE in HCAO sera circulate together in a 50 kD complex. Several lines of evidence suggest that in this form, IGFBP2 facilitates the transport of IGFIIE or IGFII to skeletal tissue. Concomitant infusion of IGFBP2 with IGFI or II in goats increased the clearance of IGFI and -II, and at the same time reduced the transfer of IGFs into breast milk, suggesting that IGFBP2 facilitated the transit of the IGFs out of the circulation, and away from the mammary epithelium. The findings in the HCAO patients and the in vitro data suggest that this other tissue is the skeleton. A potential mechanism for the selective transport of IGFIIE (and possibly IGFII) to the bone matrix of HCAO patients is suggested as IGFs, and especially IGFII, enhance IGFBP2 binding to the extracellular matrix produced by human osteoblasts. IGF/IGFBP2 complex has been shown to bind the extracellular matrix produced by fibroblasts. Binding of IGFBP2 was principally to glycosaminoglycans, which are abundant in the bone matrix.

Pharmaceutical Compositions

The invention also features a pharmaceutical composition including an amount of IGFII polypeptide and IGFBP2 polypeptide effective to increase bone mass in a mammal and a pharmaceutically acceptable carrier. Useful IGFII polypeptides include IGFII, IGFIIE, and IGFI containing a heparin-binding motif The amount of IGFII polypeptide and IGFBP2 polypeptide effective to increase bone mass in a mammal may vary, depending on a number of factors, including the preferred dosage of the complex to be administered, the chemical characteristics of the polypeptides employed, the formulation of the complex excipients and the route of administration. The dosage of a pharmaceutical composition to be administered can be adjusted by the practitioner to account for such variables as the overall health status of the particular patient and the relative biological efficacy of the compound selected. For example, from about 0.01 mg/kg/day to about 10 mg/kg/day of the pharmaceutical composition can be administered to a patient.

IGFII polypeptide and IGFBP2 polypeptide can be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration.

The invention also features an article of manufacturing including packaging material and a pharmaceutical agent contained within the packaging material. The pharmaceutical agent includes a complex of an IGFII polypeptide and an IGFBP2 polypeptide, and is therapeutically effective for increasing bone mass. The packaging material includes a label or package insert that indicates that the pharmaceutical agent can be used for increasing bone mass or treating osteoporosis, for example using the methods described herein.

The invention will be further described in the following examples, which do not limit the scope of the invention described in the claims.

EXAMPLES

Example 1

General Methods:

After informed consent, overnight fasting serum samples were obtained from seven previously reported cases of HCAO. Villareal et al., *Am. J. Med.*, 93:371–381 (1992); Beyer et al, *J. Bone Miner. Res.*, 5:1257–1263 (1990); Whyte et al., *J. Bone Miner. Res.*, 11:554–558 (1996); Whyte et al., *Am. J. Med.*, 102:219–220 (1997); and Hassoun et al., *Am. J. Med.*, 103:70–73 (1997). All patients had documented acquired osteosclerosis (assessed radiologically and histologically) and serological evidence of chronic hepatitis C infection, although none had symptomatic liver disease and the hepatitis C infection tended to be an incidental clinical finding. Samples were obtained from five men and two women aged 32 to 73 years. Sera were kept either on dry ice or at −70° C. until analyzed. Control groups included normal healthy individuals (n=9, age range 36 to 71 years), hepatitis C patients without clinical or radiologic evidence of osteosclerosis (n=9, age range 22 to 70 years), hepatitis B patients (as a control for an unrelated liver disease) (n=6, age range 23 to 51 years), and patients with Paget bone disease (as a control for increased bone formation unrelated to hepatitis C infection) (n=5, age range 54 to 71 years).

Production and Isolation of Bovine IGFBP2:

To express the bovine IGFBP2 protein a previously described cDNA coding for the protein (Upton, F. Z. et al., *J. Mol. Endocrinol.*, 5:77–84 (1990)) was inserted into the mammalian expression plasmid pRSVN (McKinnon P. et al., *J. Mol. Endocrinol.*, 6:231–239 (1991)). This plasmid was introduced into the CHO K1 cell line by electroporation. Neomycin resistant clones were isolated and screened for secretion of bovine IGFBP2 protein into the media by ELISA assay with a monoclonal antibody raised against bovine IGFBP2. A single clone designated as 1C1 was selected for production of bovine IGFBP2 protein.

Conditioned media containing IGFBP2 protein was generated by culture of the 1C1 CHO cells in a Cell Factory (Nunc) in DMEM/F12 media plus 2% FBS to confluence and switched to serum-free DMEM/F12 for production. Conditioned media was stored at −20° C. in the presence of 0.5% Tween 20. Purification of IGFBP2 protein was achieved by an initial purification by affinity chromatography with human IGFI protein (GroPep) coupled to Affi-prep 10 media (Bio-Rad) according to manufacturer's instructions. The IGFBP2 containing supernatants were passed twice over the affinity column, washed with 50 mM sodium phosphate, 150 mM NaCl, pH 6.5 and eluted with 0.5 M acetic acid. Peak protein-containing fractions, identified by analytical HPLC, were pooled and adsorbed on a C4 Delta-Pak HPLC column (Waters) in the presence of 0.1% TFA and eluted with a 28% to 44% acetonitrile gradient with 0.1% TFA as the counter-ion. Peak protein fractions were again pooled and loaded onto a Hi Load Q column (Pharmacia) in the presence of 20 mM Tris-HCl, pH 7.2 (buffer A). The IGFBP2 protein was eluted with a 0–100% gradient of 150 mM NaCl in buffer A over 100 min. This step resolved several processing variants of the IGFBP2 protein. The mature IGFBP2 protein was then identified by pH 3.0 to pH 9.0 isoelectric focusing gel electrophoresis analysis of peak protein-containing fractions (pharmacia Phast System).

The identity and purity of the IGFBP2 protein was confirmed by analysis on 10–20% Tris-glycine polyacrylamide gels (Novex) and N-terminal sequence analysis. Mass spectrometry showed the expected molecular weight of about 31 kD. Western ligand blot analysis showed that the IGFBP2 protein was able to bind IGFII.

Production and Isolation of IGFIIE:

To express the full-length IGFIIE protein in bacteria the expression plasmid pMpGH(1–46)VNG/IGFII, encoding the mature version of IGFII cDNA with a 46 amino acid growth hormone leader sequence (as detailed in U.S. Pat. No. 5,330,971) and a glycine in the first position of the IGFII molecule (Whitfield H. J. et al., *Nature*, 312:277–280 (1984)), was modified as follows. This plasmid was used as a template for a polymerase chain reaction (PCR) extension technique to add nucleotides corresponding to the E-domain of IGFII optimized for expression in bacteria. The following DNA oligonucleotide primers were synthesized:

| Primer | Primer Sequence | SEQ ID |
|---|---|---|
| 1714 | 5' TCAGGCTGAAAATCTTCTCTC 3' | 1 |
| IIE/1 | 5' CGGGTAACGCGGGAAGTTGTCCGGCAGAACAGTCGGCG GAGTAGAAACGTCACGCTCGGACTTGGCGGG 3' | 2 |
| IIE/2 | 5' ACGCAGACGCTGAGTAGACTGTTTCCAAGTGTCGTACT GGAAGAATTTACCAACCGGGTAACGCGGGAA 3' | 3 |
| IIE/3 | 5' CTCCAGTTCTTTAGCCAGAACGTGACCACGACG AGCACGCAGCAGAGCCGGCAGACCACGACGCAGACGCTG AGT 3' | 4 |

-continued

| Primer | Primer Sequence | SEQ ID |
|---|---|---|
| IIE/4 | 5'GTCCTGAGTCGGCAGAGCGATCAGCGGACGGTGACGTT TAGCTTCACGGAAAGCCTCCAGTTCTTTAGC 3' | 5 |
| IIE/5 | 5'CTAGATAAGCTTTCATCATTTACGGTTAGAAGC CATTTCCGGCGGAGCACCACCGTGAGCCGGGTCCTGAGTC GGCAG 3' | 6 |

The Expand high Fidelity PCR System (Boehringer Mannheim) and primer #1714 and IIE/1 were then used to amplify a product from the plasmid pMpGH(1–46)VNG/IGFII. The product was purified by standard techniques and used as the template for PCR amplification with primer #1714 and IIE/2. Successive rounds of amplification followed with primer #1714 and the IIE/3, IIE/4 and IIE/5 primers to generate a final product coding for the complete prepro-IFG-IIE protein. This PCR fragment was digested with HpaI and HindIII and subdloned into a HpaI-HindIII restricted pMpGH(1–46)VNG/IGFII vector to replace the IGFII cDNA with the IGFIIE cDNA.

The sequence of the IGFIIE insert in the resulting plasmid was confirmed by DNA sequence analysis using the Thermo Sequenase terminator cycle sequencing kit (Amersham) according to the manufacturer's instructions. This bacterial expression plasmid contains a cDNA encoding the full length IGFIIE sequence with a glycine at position-1 of the IGF protein immediately downstream of a hydroxylamine cleavage site and a 46 amino acid growth hormone leader peptide sequence and is hereafter referred to as pGH(46)/IGFIIE.

For protein expression the pGH(46)/IGFIIE plasmid was introduced into the *E. coli* strain BL21 (Stratagene) according to the supplier's instructions. A pGH(46)/IGFIIE transformed colony was inoculated into Luria Bertani (LB) medium and cultured overnight. An aliquot was transferred to a fresh sample of LB medium and incubated at 37° C. until an absorbance ($A_{600}$) of 0.6 was reached. At this time isopropyl β-D-thiogalactopyranoside (IPTG) was added to a final concentration of 0.2 mM, to induce the cells to the produce the IGFIIE fusion protein as inclusion bodies (IBs). Following further incubation, the culture was centrifuged to pellet the cells, and after removal of the supernatant, the cells were lysed with SDS-PAGE lysis buffer (Novex). These cultures were compared directly with cultures derived from parental BL21 cells, lacking the IGFIIE expression plasmid, by SDS-PAGE chromatography employing 10–20% Tris-Glycine gels (Novex) to confirm expression of the IGFIIE fusion protein. A clone identified as expressing the fusion protein was used in a scale-up process to produce appropriate quantities of the fusion protein for in vitro and in vivo experiments.

Two 5 liter Applikon fermenters were used, each containing 3L of LB medium supplemented with glucose (12% w/v) and MgSO$_4$ (0.12% w/v). The media was inoculated with an aliquot of a log phase culture of BL21 cells expressing the IGFIIE fusion protein. Inoculated fermentation cultures were incubated at 37° C. overnight. At an absorbance at 600 nm ($A_{600}$) of between 4–6, IPTG was added to the cultures to a final concentration of 0.2 mM and the cells further incubated until an $A_{600}$ of approximately 15–20 was reached, after which the fermentation suspension was subjected to four passes through a homogenizer. This process disrupted the cells, facilitating the further isolation and purification of IBs by four centrifugation and washing steps, using 30 mM NaCl/10 mM KH$_2$PO$_4$ washing buffer. A final yield of 14.5 grams of wet IB's was obtained and was stored at −20° C.

The IB pellet containing the IGFIIE fusion protein was solubilized, desalted and refolded by conventional methods. The IGFIIE fusion protein was then isolated and cleaved, followed by chromatographic steps, employing variations of known methods. These processes included, in sequence:

1) dissolution of IBs in buffer (8M urea, 0.1M Tris, 40 mM glycine, 0.5 mM NzCl$_2$ and 16 mM dithiothreitol (DTT) pH 9.0), centrifugation and filtration (1 μm gradient Whatman filter) to remove particulate contaminants and desalting into 8M urea, 0.1M Tris, 40 mM glycine, 0.5 mM ZnCl$_2$ and 1.6 mM DTT pH 9.0 by size exclusion chromatography on Cellufine GCL-1000M.

2) A 195 ml pool of buffer containing approximately 180 mg of fusion protein was reconstituted to 5L in 4 M urea, 20 mM glycine, 0.1 M Tris, 0.4 mM DTT and 0.5 mM ZnCl$_2$, pH 9.0; refolded over 180 minutes with the addition of 2-hydroxyethyl disulphide to 1 mM. The mixture was re-acidified to pH 2.5 with concentrated HCl to stop the reaction.

3) The 5L refolding mixture was diluted to 10 L with a cleavage buffer containing 4 M urea, 20 mM glycine, 0.1 M Tris and 2 M NH$_2$OH. The pH was adjusted to pH 8.65 and incubated for 16 hrs at 37° C.

4) After filtration through a 0.8 μm filter (Millipore), the clarified mixture was chromatographed using reverse-phase high performance liquid chromatography (RP-HPLC) employing a 40 mm diameter, 100 mm long C4 column (Waters) washing with 0.1% heptafluorobutyric acid (HFBA) and eluting with 80% acetonitrile/0.1% HFBA.

5) A final desalting and purification was performed using RP-HPLC and the C4 column but employing a 0.1% heptafluorobutyric acid (HFBA) wash and elution with 80% acetonitrile/0.1% HFBA gradient at 0.16% per minute.

Dissolution, refolding and cleavage of IGFIIE fusing protein derived from the pGH(46)-IGFIIE expression vector construct in the foregoing manner yielded material that exhibited IGF receptor binding activity. SDS-PAGE analysis showed that the protein ran as a major band of 17.6 kD with additional minor lower molecular weight forms.

IGF/IGFBP Measurements:

IGFI and IGFII were measured by specific radioimmunoassays (RIA) after separation from IGFBPs by G-50 acid chromatography as described previously. Powell et al., *Clin. Endocrinol. Metab.*, 63:1186–1192 (1986). IGFIIE was measured by a previously validated RIA using an antibody generated against a synthetic 16-amino acid segment of the predicted IFG-II E-domain (E-II$_{69-84}$). E-II$_{69-84}$ was used as radioligand and for the standard curve. Liu et al., *J. Clin. Endocrinol. Metab.*, 76:1095–1100 (1993). This assay is specific for proteins with the E-II domain and does not detect the mature form of IGFII. IGFBP3 levels were measured by RIA as previously described using covalent [$^{125}$I] IGFII:IGFBP3 as tracer. Liu et al., *J. Clin. Endocrinol. Metab.*, 75:1261–1267 (1992). IGFBP2 levels were assayed by RIA with a polyclonal anti-IGFBP2 antibody (1:2000 final dilution) provided by Dr. Werner Blum (Tubingen, Germany). Recombinant human IGFBP2 was used for the tracer and the standard curve (Austral, San Ramon, CA). IGFBP-1 was measured by a two-site immunoradiometric assay and ALS by immunosorbent assay (Diagnostic Systems Laboratories, Webster, Tex.).

Column Chromatography:

Sephadex G-50 column chromatography in acid was performed as previously described. Liu et al., 1993, supra. Briefly, patient or normal serum (1 mL) was fractionated on a 1×120 cm G-50 Sephadex column (Pharmacia, Piscataway, N.J.) in 1% formic acid. Five mL fractions were collected, lyophilized, and then redissolved in RIA buffer. For Superdex 200 (S-200) chromatography, a 1×120 cm S-200 (Pharmacia, Piscataway, N.J.) column was equilibrated in 0.1 M Tris/HCl with 0.15 m NaCl, pH 7.4 buffer, and 0.5 mL of each serum sample was fractionated at a flow rate of 0.5 mL/min. Two mL fractions were collected, and the IGFs and IGFBPs assayed as described above. Columns were calibrated with aldolase (158 kD), ovalbumin (43 kD), myoglobin (19 kD), cytochrome c (12.4 kD), and IGFI and -II (~7 kD).

Western Ligand Blotting:

Western ligand blot analysis for IGFBPs was performed as previously described. Hassager et al., *J. Clin. Endocrinol. Metab.*, 75:228–233 (1992). Briefly, 1 gL of serum or 50 μL of extracellular matrix sample (see below) was separated by sodium dodecyl sulfate-polyacrylamide gel electrophoresis (SDS-PAGE) with a 7.5% to 15% linear gradient under nonreducing conditions. The separated proteins were electroblotted onto nitrocellulose filters, and the filters were then blocked, probed with $^{125}$-labeled IGFII overnight at 4° C., and visualized by autoradiography according to the method of Hossenlopp et al., *Anal. Biochem.*, 154:138–143 (1986). Scanning densitometry and molecular size determinations were performed using an UltraScan XL laser densitometer and Gel-Scan XL software (Pharmacia LKB Biotechnology, Uppsala, Sweden).

IGFBP-2 Binding to Extracellular Matrix:

Binding assays were performed using extracellular matrix derived from normal adult human osteoblastic cells or fetal human osteoblastic cells immortalized with a temperature-sensitive T antigen. Robey et al., *Calcif. Tissue Int.*, 37:453–460 (1985) and Harris et al., *J. Bone Miner. Res.*, 10:178–186 (1995). Cells were grown to confluency in 24-well plates (Primera, Falcon Laboratories, Logan Vt.). Monolayers were washed and the cells were removed. Atria et al., *Endocrinology*, 137:4571–4575 (1996). The extracellular matrix, which remained on the plates, was used for the binding studies.

In one set of experiments, extracellular matrix was incubated overnight at 4° C. with rhIGFBP2 (500 ng/mL, Sandoz Pharmaceuticals, Basel, Switzerland) in the absence or presence of 400 ng/mL IGFI, IGFII, or insulin. Extracellular matrix proteins were extracted and IGFBP content determined by Western ligand blotting. In a second set of experiments, extracellular matrix-coated wells were incubated overnight at 4° C. with $^{125}$I-rhIGFBP2 (50,000 cpm; 5 μCi/μg) in the absence or presence of unlabeled IGFI, IGFII, or insulin. Extracellular matrix was extracted and counted in a gamma counter (ICN Micromedic Systems, Huntsville, Ala.). Nonspecific binding was defined as the amount of $^{125}$I-rhIGFBP2 bound in the presence of 400 ng/mL unlabeled IGFBP2. Nonspecific binding was subtracted from total binding to determine specific binding.

Human Osteoblast Proliferation Studies:

Proliferation studies using normal adult human osteoblasts were performed as described previously. Conover, C. A., *J. Clin. Invest.*, 88:1354–1361 (1991); Durham, S. K. et al., *J. Bone Miner. Res.*, 9:111–117 (1994). In brief, adult human osteoblastic cells were plated in 24-well plates and grown for either 1 day or for 10 days. Cells were washed and changed to serum-free medium without or with 10 nM of IGFII, IGFBP2, or the combination. [$^3$H]Thymidine incorporation was measured at 22–26 hours.

Statistical Analysis:

Overall group differences were assessed using analysis of variance (ANOVA). When the ANOVA was statistically significant (P<0.05), individual comparisons were performed using non-paired two-sided t-tests. Data are presented as mean±SEM.

Example 2

Serum Levels of IGFs/IGFBPs/ALS:

Table 1 presents serum levels of IGFs, IGFBPs, and ALS in HCAO patients and four control groups. Serum levels of IGFI and -II were not altered in HCAO and were not significantly different among the groups. Immunoreactivity for the E-peptide domain of IGFII was elevated approximately 2.6-fold in HCAO, into the range of values previously reported for patients with NICTH using this assay. IGFIIE levels were also elevated in hepatitis C patients without osteosclerosis, but not in hepatitis B patients. Among the viral hepatitis patients, therefore, IGFIIE elevations were specific for the two groups of hepatitis C patients. However, this abnormality was not unique to the hepatitis C patients, because IGFIIE levels were also elevated in patients with Paget bone disease.

TABLE 1

Serum levels of IGFs and IGFBPs in HCAO and control groups (mean ± SEM, all in μg/L.)

| | IGFI | IGFII | IGFII E | IGFBP-I | IGFBP2 | IGFBP3 |
|---|---|---|---|---|---|---|
| Normals (n = 9) | 228 ± 27 | 657 ± 55 | 2.7 ± 0.1 | 30 ± 9 | 377 ± 44 | 2274 ± 195 |
| HCAO (n = 7) | 190 ± 18 | 505 ± 60 | 7.1 ± 1.0$^a$ | 52 ± 11 | 803 ± 159$^b$ | 1354 ± 196$^c$ |
| Hepatitis C controls (n = 9) | 207 ± 20 | 598 ± 25 | 5.4 ± 0.2$^a$ | 31 ± 9 | 353 ± 61 | 1505 ± 121$^c$ |
| Hepatitis B controls (n = 6) | 195 ± 35 | 546 ± 142 | 2.3 ± 0.2 | 90 ± 54 | 320 ± 32 | 1595 ± 269$^d$ |
| Paget's disease (n = 5) | 129 ± 6 | 669 ± 38 | 6.7 ± 0.2$^a$ | 14 ± 4 | 291 ± 75 | 2364 ± 328 |
| ANOVA (P-value) | 0.13 | 0.42 | <0.001 | 0.21 | 0.001 | 0.004 |

$^a$P < 0.001 vs normals,
$^b$P < 0.02 vs normals,
$^c$P < 0.01 vs normals,
$^d$P = 0.06 vs normals The IGFIIE domain immunoreactivity in the sera of the HCAO patients was further characterized using Sephadex G-50 acid chromatography. Data from two of these patients are shown in FIG. 1. The IGFIIE immunoreactivity in the HCAO sera had a molecular weight of approximately 10–20 kD, with some size heterogeneity, as has previously been reported for IGFII prohormone. There was no evidence for low molecular weight E-domain fragments in the sera of these patients. Similar molecular weight estimates of 15 kD for the IGFIIE immunoreactivity were obtained by immunoblotting HCAO sera with IGFII antibody. Thus, the IGFIIE domain immunoreactivity in sera of HCAO patients corresponded to the intact IGFII prohormone or IGFIIE.

Table 1 also presents immunoassayable levels of IGFBP-1, IGFBP2, IGFBP3, and ALSs in the HCAO and control groups. IGFBP-1 levels were not significantly different among the groups. IGFBP3 and ALS levels were lower in the hepatitis C and B patients compared to either the normal subjects or the patients with Paget bone disease. The unique abnormality in the HCAO patients, however, was a marked increase in IGFBP2 levels (Table 1). The immunoassay data were confirmed by Western ligand blot analysis of HCAO versus normal sera, which also demonstrated the significant increase in IGFBP2 in these patients at the expected molecular size for the intact protein on SDS-PAGE (~34 kD). The Western ligand blot data were independently verified by immunoprecipitating with IGFBP2 antibody. Immunoreactive IGFBP2 in HCAO sera was confirmed to be intact protein by Biogel P-60 acid chromatography as well as by non-denaturing S-200 chromatography (see FIG. 3). While IGFBP-4 levels were not measured by immunoassay. The Western ligand blot indicated that there was no apparent difference in IGFBP-4 levels between HCAO and normal subjects.

The Western ligand blot also showed the decrease in serum IGFBP2 levels between 1993 and 1996 in one of the HCAO patients who had clinical remission of bone pain over this time period. This remission was associated with a decrease in serum levels of liver enzymes (aspartate aminotransferase) as well as in markers of bone formation (alkaline phosphatase, osteocalcin). The biochemical changes were also associated with a marked decline in both serum IGFBP2 and IGFIIE to levels indistinguishable from the mean for the normal subjects (Table 2). Treatment during this period consisted of subcutaneous calcitonin and bisphosphonates (intravenous pamidronate followed by oral etidronate) in an attempt to decrease bone turnover. Since increased bone turnover per se, as present in the Paget's patients, did not result in significant elevations in IGFBP2 levels (Table 1), the decline in IGFBP2 levels over this time period was likely related to the course of the disease, perhaps due to remission of the liver disease, rather than to a non-specific effect of a decrease in bone turnover.

TABLE 2

Changes over time in serum aspartame aminotransferase (AST), alkaline phosphatase, osteocalcin, IGFIIE, and IGFBP 2 levels in a patient with HCAO.

|  | Nov. 1993 | Oct. 1996 |
|---|---|---|
| AST, U/L[a] | 68 | 34 |
| Alkaline phosphatase, U/L[b] | 3187 | 248 |
| Osteocalcin, µg/L[c] | 219 | 60 |
| IGFIIE, µg/L | 7.2 | 1.6 |
| IGFBP2, µg/L | 862 | 372 |

Figure 2:
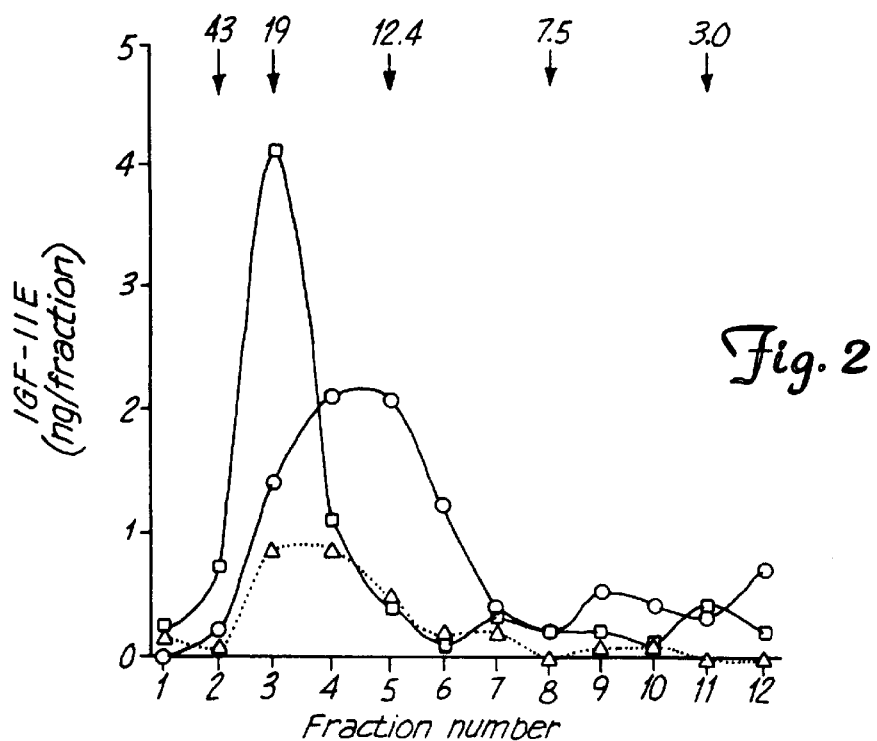
FIG. 2 are chromatograms from the fractionation of (A) IGFBP3, (B) IGFI, and (C) IGFII from sera of two HCAO patients (♦—♦, •—•) and from a control subject (▲—▲). The arrows indicate the elution volume of proteins used as molecular size markers, with the numbers indicating the size in kD.

[a]Reference range, 12–31 U/L
[b]Reference range, 98–257 U/L
[c]Reference range, 8.8–29.7 µg/L Example 3
Distribution of Serum IGFs and IGFBPs Between 150 kD and 50 kD Complexes:

In addition to measuring serum levels of the IGFs and IGFBPs, the distribution of the IGFs bound to IGFBPs in the ~150 kD and ~50 kD complexes in HCAO serum was assessed by S200 column chromatography (FIG. 2). IGFBP3 is the only binding protein that forms a 150 kD ternary complex with IGF and ALS. As shown in FIG. 2A, most of the IGFBP3 in the HCAO serum was found in the 150 kD complex, as is the case for normal serum. Essentially all of the IGFI in HCAO serum was associated with IGFBP3 in the 150 kD complex, and this distribution of IGFI did not differ between HCAO and normal serum (FIG. 2B). Nearly all of the IGFII in normal serum was also in the 150 kD fraction, and although most of the IGFII in HCAO serum was in the 150 kD fraction, there was some increase in IGFII in the 50 kD fraction in HCAO compared to normal serum (FIG. 2C).

Figure 3A:
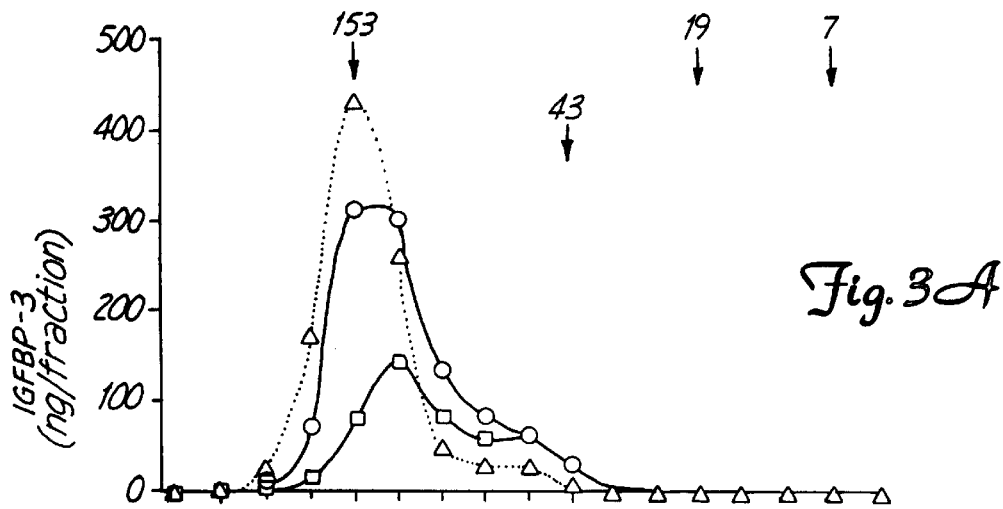
FIG. 3 is a chromatogram from the fractionation of (A) IGFBP2 and (B) IGFIIE from sera of two HCAO patients (♦—♦, •—•) and a control subject (▲—▲). The arrows indicate the elution volume of proteins used as molecular size markers, with the numbers indicating the size in kD.
Figure 3B:
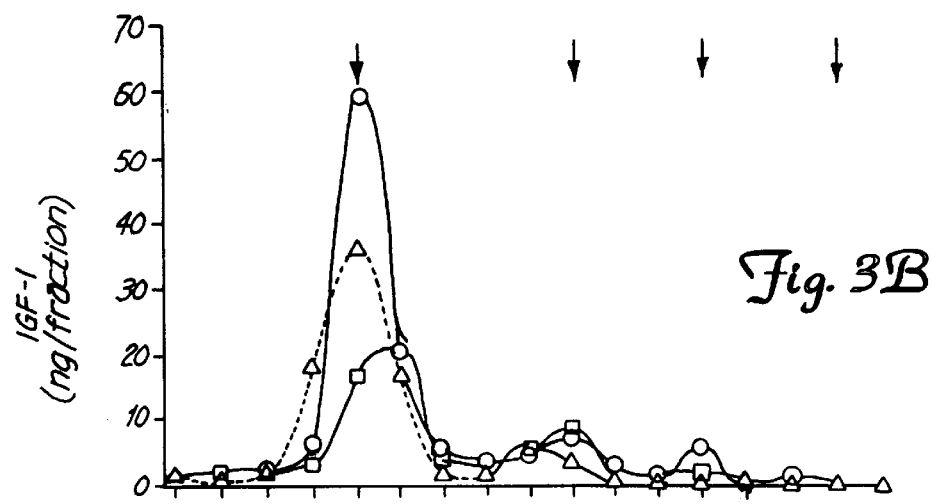
Figure 3C:
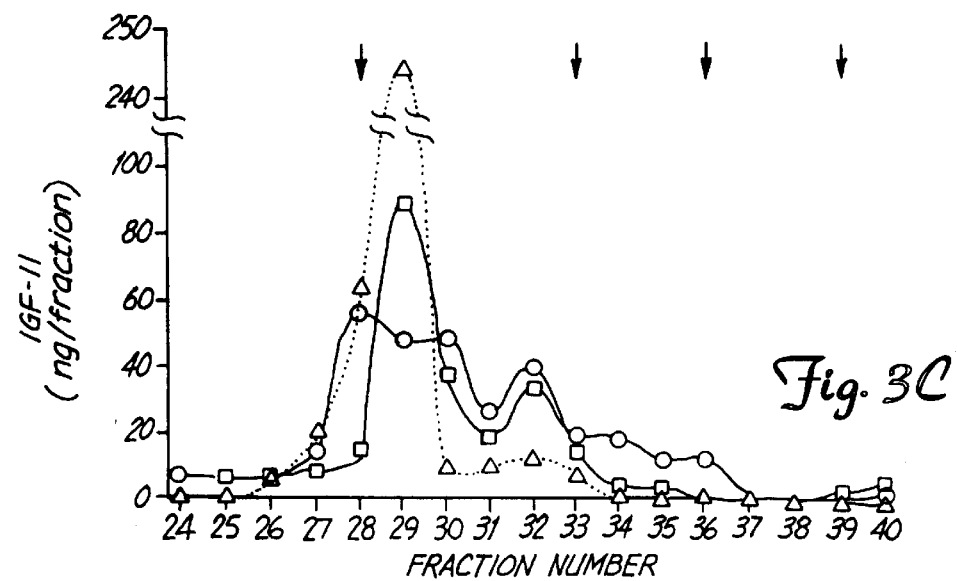

All of the IGFBP2 in the HCAO patients' as well as normal sera was in the 50 kD fraction. However, the absolute amount of IGFBP2 was significantly increased in the patient sera (FIG. 3A). There was no evidence by S-200 chromatography of low molecular fragments of IGFBP2 in HCAO sera. Moreover, as shown in FIG. 3B, the majority of IGFIIE in the patient and control serum was also found in the 50 kD complex, presumably in association with IGFBP2, which is the principal component of this complex. In HCAO serum, there was some evidence for IGFIIE in the 150 kD complex as well.

Example 4
In Vitro Studies on IGFBP2 Interactions with the Extracellular Matrix of Human Osteoblasts:

The above in vivo data indicated not only that HCAO patients had an increase in both intact IGFIIE and IGFBP2, but also that the two proteins circulated together in the 50 kD IGF/IGFBP complex. To determine if IGFBP2 could facilitate the transport of IGFII and/or IGFIIE to bone matrix in these patients, it was assessed whether the IGF/IGFBP2 complex could bind to human bone matrix in vitro. rhIGFBP2 (500 ng/mL) was incubated overnight at 4° C. with human osteoblast-derived extracellular matrix in the presence or absence of 400 ng/mL of IGFI, IGFII, or insulin. The extracellular matrix was washed with rhIGFBP2 binding determined by Western ligand blot of solubilized matrix. Extracellular matrix incubated without IGFs showed minimal binding of rhIGFBP2. In the presence of IGFI or IGFII, however, the binding of rhIGFBP2 to extracellular matrix was significantly enhanced. By densitometry, rhIGFBP2 binding to the osteoblast extracellular matrix was increased 2-fold in the presence of IGFI, whereas rhIGFBP2 binding was increased over 3-fold in the presence of IGFII. Insulin, which is structurally related to the IGFs but does not bind IGFBPs, did not enhance rhIGFBP2 binding to the osteoblast extracellular matrix. In the absence of exogenous rhIGFBP2, there was little or no endogenous IGFBP present in the osteoblast extracellular matrix. These findings were confirmed in another set of experiments that measured specific $^{125}$I-rhIGFBP2 binding to the extracellular matrix produced by human osteoblasts. As shown in Table 3, unlabeled IGFI increased specific $^{125}$I-rhIGFBP2 binding to the osteoblast extracellular matrix by approximately 2-fold, whereas the same concentration of IGFII increased $^{125}$I-rhIGFBP2 binding by over 4-fold. The converse experiment yielded similar findings, i.e., $^{125}$I-IGFII alone did not bind extracellular matrix components (0.05±0.05%), whereas in the presence of unlabelled rhIGFBP2, $^{125}$I-IGFII specific binding was 2.86±0.10% (P<0.001).

TABLE 3

Percent specific $^{125}$I-rhIGFBP2 binding to the extracellular matrix of human osteoblasts (n = 3 independent experiments).

|  | Percent specific binding |
|---|---|
| $^{125}$I-rhIGFBP2 alone | 0.73 ± 0.08 |
| $^{125}$I-rhIGFBP2 + IGFI | 1.31 ± 0.11[a] |
| $^{125}$I-rhIGFBP2 + IGFII | 3.13 + 0.30[b] |

[a]P = 0.01 vs $^{125}$I-rhIGFBP alone
[b]P = 0.002 vs $^{125}$I-rhIGFBP alone

Figures 4A, 4B:
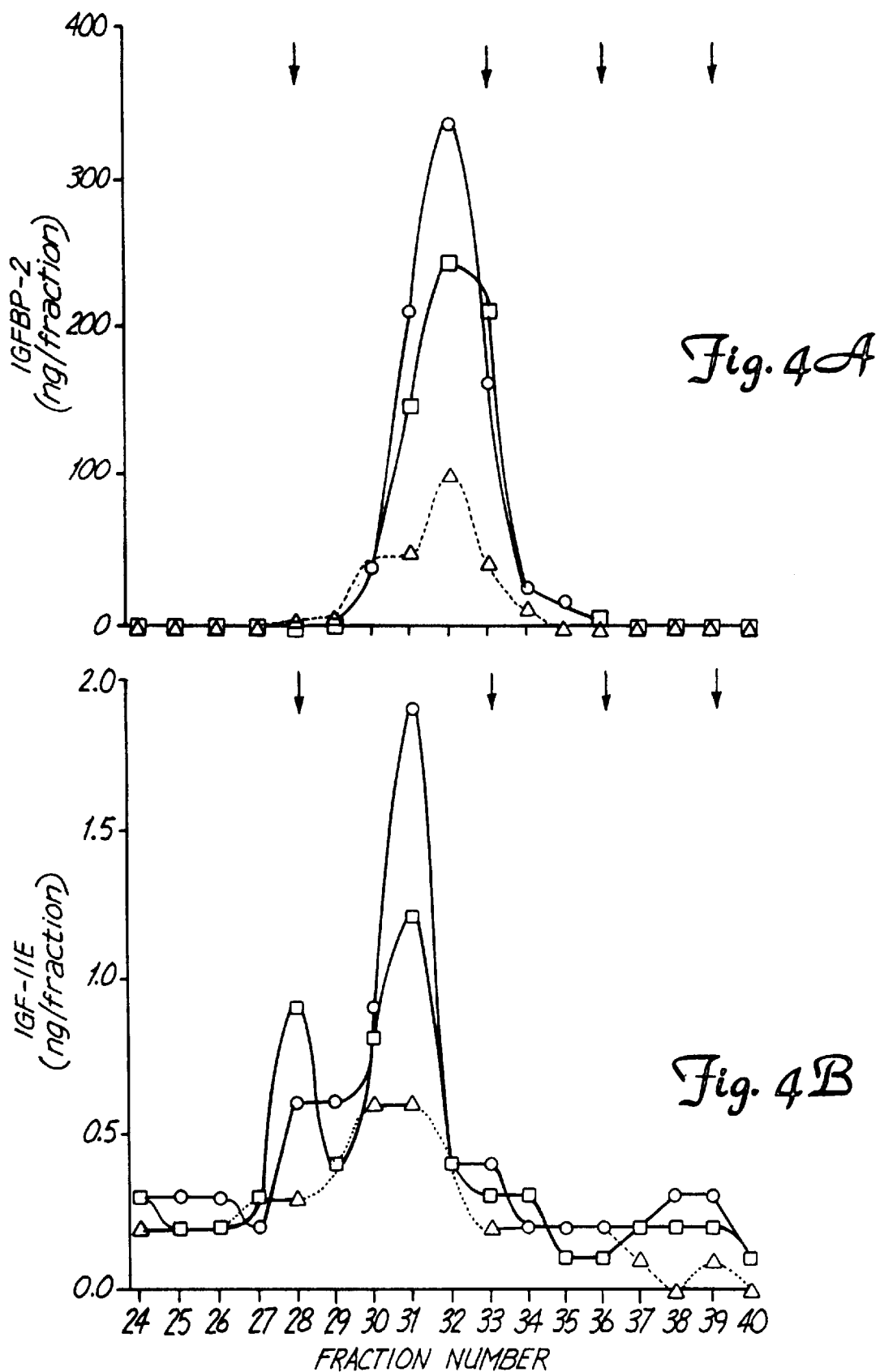
FIG. 4 is a graph that depicts the effects of IGFBP2 on IGFII (both at 10 nM) stimulation of osteoblast proliferation in cells cultured either for 1 day or for 10 days prior to stimulation with IGFII or IGFII+IGFBP2. Data are expressed as the percent of maximal IGFII stimulation (mean+SEM of three experiments). *, P<0.001 versus IGFII alone.

Example 5
Studies Assessing IGFBP2 Effects on IGFII Stimulation of Osteoblast Proliferation:

The above studies indicated that IGFBP2 could facilitate the transport of IGFII and/or IGFIIE to bone matrix in HCAO patients. To test whether the IGFII/IGFBP2 complex could stimulate human osteoblast proliferation and to assess the potential role of extracellular matrix in modulating this effect, IGFII versus IGFII+IGFBP2 stimulation of human osteoblast proliferation was compared either 1 day after plating or 10 days after plating. These cells have been shown to progressively produce extracellular matrix in vitro and, in fact, form mineralized nodules with continuous culture under appropriate conditions. Thus, the 1 day cultures represent a relatively extracellular matrix-poor environment, whereas the 10 day cultures represent a relatively extracellular matrix-rich environment. Under both conditions, IGFII markedly stimulated osteoblast proliferation: the percent [$^3$H]thymidine incorporation increased following stimulation with IGFII from 0.12+0.003% to 0.74±0.086% in the 1 day cultures (P<0.005), and from 0.98±0.08% to 2.06±0.12% (P<0.005) in the 10 day cultures. As shown in FIG. 4, however, while IGFBP2 markedly inhibited (by 80%) IGFII stimulation of osteoblast proliferation in the 1 day cultures, the IGFII/IGFBP2 complex was as effective as IGFII in stimulating osteoblast proliferation in the 10 day cultures. IGFBP2 alone had no effect on osteoblast proliferation under either condition.

Example 6
Specific Binding of IGFBP2 to Bone Cell-derived Extracellular Matrix and Heparin-Sepharose:

$^{125}$I-IGFBP2 was incubated without ($B_o$) and with IGF (IGFI, IGFII, IGFIIE or IGFIs2) overnight at 4° C. with ECM prepared from human osteoblasts (hOB) and rat osteosarcoma cells (UMR, ROS), and with heparin-Sepharose (Hep-Seph) and Sepharose (Seph) beads. IGFIs2 is IGFI containing a heparin binding motif. Nonspecific binding (in the presence of excess unlabeled IGFBP2) was subtracted from total binding to get percent specific $^{125}$I-IGFBP2 binding shown in Table 4. Each experiment was performed in triplicate.

As shown in Table 4, IGFs enhanced IGFBP2 binding to ECM. IGFIIE provided the greatest increase in IGFBP2 binding to ECM and heparin-sepharose, followed by IGFII, IGFIs2 and IGFI. IGFs increased the binding to ECM derived from humans as well as rat osteoblastic cells. The binding appeared to be specific for heparin-sepharose suggesting that in vivo, binding is to heparin sulfate moieties within glycosaminoglycans of the extracellular matrix.

TABLE 4

Percent Specific $^{125}$I-IGFBP2 Binding

| | $B_o$ | +IGFI | +IGFII | +IGFIIE | +IGFIs2 |
|---|---|---|---|---|---|
| hOB ECM | <0.1 | — | 1.1 | 1.8 | — |
| UMR ECM | <0.1 | 0.5 | 1.2 | — | — |
| ROS ECM | <0.1 | 0.6 | 1.2 | — | — |
| Hep-Seph | 0.2 | 3.8 | 14.6 | 55.5 | 8.5 |
| Seph | <0.1 | <0.1 | <0.1 | 0.1 | <0.1 |

Specific binding of IGFBP2 (human vs. bovine) to human osteoblast-derived extracellular matrix (ECM) was assessed as follows. Human or bovine forms of IGFBP2 (500 ng/ml) without (Control) and with 400 ng/ml IGFI, IGFII, or insulin (Ins) were incubated overnight, 4° C. with ECM derived from human osteoblasts in culture. ECM was washed, and proteins were extracted and analyzed for IGFBP content by Western ligand blotting with $^{125}$I-IGFII. Human and bovine IGFBP2 binding to ECM was enhanced by IGFII. Similar experiments were performed with the exception that IGFBP-1, -2, and -6 (500 ng/ml) were incubated with heparin-Sepharose without (Control) and with 400 ng/ml IGFII, IGFIs2, IGFI. Of the six IGFBPs tested, IGFII specifically enhanced IGFBP2 binding to matrix. Similar results were obtained with the IGFI analog IGFIs2.

Example 7
Effect of IGFBP2 on IGFII Stimulation of Proliferation of Different Cell Types in Culture:

IGF-responsive human cell types [normal osteoblasts (hOB), normal skin fibroblasts (HF), breast cancer cells (MCF-7), ovarian cancer cells (OV266)] were stimulated with 10 nM IGFII, 10 nM IGFBP2, or the combination. $^3$H-Thymidine incorporation was measured as an index of proliferative response. Results shown in Table 5 are reported as the mean±S.E.M. of three determinations. Equimolar IGFBP2 had no effect on IGFII-stimulated $^3$H-thymidine incorporation in normal osteoblasts and fibroblasts, but inhibited IGFII stimulation in human breast and ovarian cancer cells by −90%. The IGFII/IGFBP2 complex may be biologically active only in certain extracellular environments, such as bone.

TABLE 5

Percent $^3$H-Thymidine Incorporation

| | Control | IGF | IGFII + IGFBP2 | IGFBP2 |
|---|---|---|---|---|
| hOB | 0.41 ± 0.08 | 1.96 ± 0.04* | 2.11 ± 0.19* | 0.43 ± 0.05 |
| HF | 0.30 ± 0.03 | 1.85 ± 0.02* | 1.95 ± 0.16* | 0.75 ± 0.09* |
| MCF-7 | 5.8 ± 0.26 | 19.6 ± 0.23* | 8.0 ± 0.14‡ | 6.5 ± 0.25 |
| OV266 | 9.8 ± 0.23 | 38.2 ± 0.75* | 12.6 ± 0.15‡ | 10.2 ± 0.46 |

*Significantly different from Control.
‡Significant effect of IGFBP2.

Example 8
Effect of IGFBP2 on IGFII Stimulation of Protein Synthesis in Normal Human Osteoblasts:

Normal human osteoblasts were treated as in Example 7, except that $^3$H-proline and $^3$H-leucine incorporation were used as measures of collagen and total protein synthesis, respectively. As shown in Table 6, equimolar IGFBP2 had no effect on IGFII stimulation of differentiated osteoblast function, i.e., matrix protein synthesis.

TABLE 6

| | $^3$H-Proline | $^3$H-Leucine |
|---|---|---|
| Control | 0.25 ± 0.006 | 1.56 ± 0.076 |
| IGFBP2 | 0.23 ± 0.003 | 1.41 ± 0.069 |
| IGFII | 0.49 ± 0.200* | 2.04 ± 0.075* |
| IGFII/IGFBP2 | 0.47 ± 0.018* | 1.91 ± 0.073* |

*Significantly different from Control.

Example 9
Targeting of Systemically-Administered IGFBP2/IGFIIE to Bone in vivo:

Female Sprague-Dawley rats (200 g) were administered approximately 2.5×106 cpm $^{125}$I-IGFBP2±unlabeled IGFIIE (4 in each group) via the iliac vein. Two hours later the animals were sacrificed, and their femurs and tibia removed, cleaned, weighed, and counted. Total cpm per gram of bone in the animals receiving $^{125}$I-IGFBP2+IGFIIE was 5770±1609 vs 3766±1259 for $^{125}$I-IGFBP2 alone (P<0.05, paired t-test). Thus, these results indicate preferential targeting of IGFBP2/IGFIIE to bone in vivo, consistent with the in vitro results.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially pure complex comprising an IGFIIE polypeptide and an IGFBP2 polypeptide.

2. The complex of claim 1, wherein said IGFIIE polypeptide and said IGFBP2 polypeptide are present in approximately equimolar amounts.

3. The complex of claim 1, wherein said IGFBP2 polypeptide is full-length IGFBP2.

4. A method of treating an osteoporosis patient comprising administering an amount of a complex comprising an IGFIIE polypeptide and an IGFBP2 polypeptide effective to increase bone mass in said patient.

5. The method of claim 4, wherein said IGFBP2 polypeptide is full-length IGFBP2.

6. A method of targeting a compound to skeletal extracellular matrix of a patient comprising administering a complex to said patient, wherein said complex comprises an IGFIIE polypeptide, an IGFBP2 polypeptide and said compound.

7. The method of claim 6, wherein said IGFBP2 polypeptide is full-length IGFBP2.

8. The method of claim 6, wherein said compound comprises a chemotherapeutic agent.

9. The method of claim 6, wherein said compound comprises a growth factor.

10. The method of claim 9, wherein said growth factor is an IGFII polypeptide.

11. The method of claim 9, wherein said growth factor is IGFI.

12. A pharmaceutical composition comprising a complex of IGFIIE polypeptide and ICFBP2 polypeptide in an amount effective to increase bone mass in a mammal, and a pharmaceutically acceptable carrier.

13. An article of manufacturing comprising packaging material and a pharmaceutical agent contained within said packaging material, wherein the pharmaceutical agent comprises a complex comprising an IGFIIE polypeptide and an IGFBP2 polypeptide and is therapeutically effective for increasing bone mass, and wherein the packaging material comprises a label or package insert which indicates that said pharmaceutical agent can be used for increasing bone mass or treating osteoporosis.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
tcaggctgaa aatcttctct c                                              21

<210> SEQ ID NO 2
<211> LENGTH: 69
<212> TYPE: DNA
<213> ORGANISM: Artificial Sequence
<220> FEATURE:
<223> OTHER INFORMATION: primer

<400> SEQUENCE: 2
cgggtaacgc gggaagttgt ccggcagaac agtcggcgga gtagaaacgt cacgctcgga     60
cttggcggg                                                            69

<210> SEQ ID NO 3
<211> LENGTH: 69
<212> TYPE: DNA
<213> ORGANISM: Artificial Sequence
<220> FEATURE:
<223> OTHER INFORMATION: primer

<400> SEQUENCE: 3
acgcagacgc tgagtagact gtttccaagt gtcgtactgg aagaatttac caaccgggta     60
acgcgggaa                                                            69

<210> SEQ ID NO 4
<211> LENGTH: 75
<212> TYPE: DNA
<213> ORGANISM: Artificial Sequence
<220> FEATURE:
<223> OTHER INFORMATION: primer

<400> SEQUENCE: 4
ctccagttct ttagccagaa cgtgaccacg acgagcacgc agcagagccg gcagaccacg     60
acgcagacgc tgagt                                                     75

<210> SEQ ID NO 5
<211> LENGTH: 69
<212> TYPE: DNA
<213> ORGANISM: Artificial Sequence
<220> FEATURE:
<223> OTHER INFORMATION: primer

<400> SEQUENCE: 5
gtcctgagtc ggcagagcga tcagcggacg gtgacgttta gcttcacgga aagcctccag     60
ttctttagc                                                            69

<210> SEQ ID NO 6
<211> LENGTH: 78
<212> TYPE: DNA
<213> ORGANISM: Artificial Sequence -continued

```
<220> FEATURE:
<223> OTHER INFORMATION: primer

<400> SEQUENCE: 6
ctagataagc tttcatcatt tacggttaga agccatttcc ggcggagcac caccgtgagc        60
cgggtcctga gtcggcag                                                     78
```